United States Patent [19]

Kelman

[11] Patent Number: 4,530,117
[45] Date of Patent: Jul. 23, 1985

[54] SURGICAL INSTRUMENT FOR AND METHOD OF INSERTING A POSTERIOR CHAMBER LENS IN AN EYE

[76] Inventor: Charles D. Kelman, N. Shore Towers, 269 Grand Central Pkwy., Bldg. 3, Floral Park, N.Y. 11005

[21] Appl. No.: 574,920

[22] Filed: Jan. 30, 1984

[51] Int. Cl.³ .................. A61F 1/16; A61F 1/24; A61F 9/00
[52] U.S. Cl. .................. 623/6; 128/303 R
[58] Field of Search .......... 3/13, 13 A; 128/1 R, 128/303 R, 339; 223/104

[56] References Cited

U.S. PATENT DOCUMENTS

| 4,190,049 | 2/1980 | Hager et al. | 128/303 R |
| 4,214,585 | 7/1980 | Bailey | 128/303 R |
| 4,429,421 | 2/1984 | Levy | 128/303 R |

Primary Examiner—W. J. Shine
Attorney, Agent, or Firm—Henry Sternberg

[57] ABSTRACT

A surgical instrument having a shank and a hook at one end of such shank with a transversely extending tip for seating the lens in the posterior chamber of the eye with the neck of the hook having a first portion adapted to extend along the anterior side of the iris, a central portion adapted to extend through the pupil and a second portion having said tip adapted to extend along the posterior side of the iris with the tip extending substantially to an inner peripheral surface of the posterior chamber of the eye.

12 Claims, 6 Drawing Figures

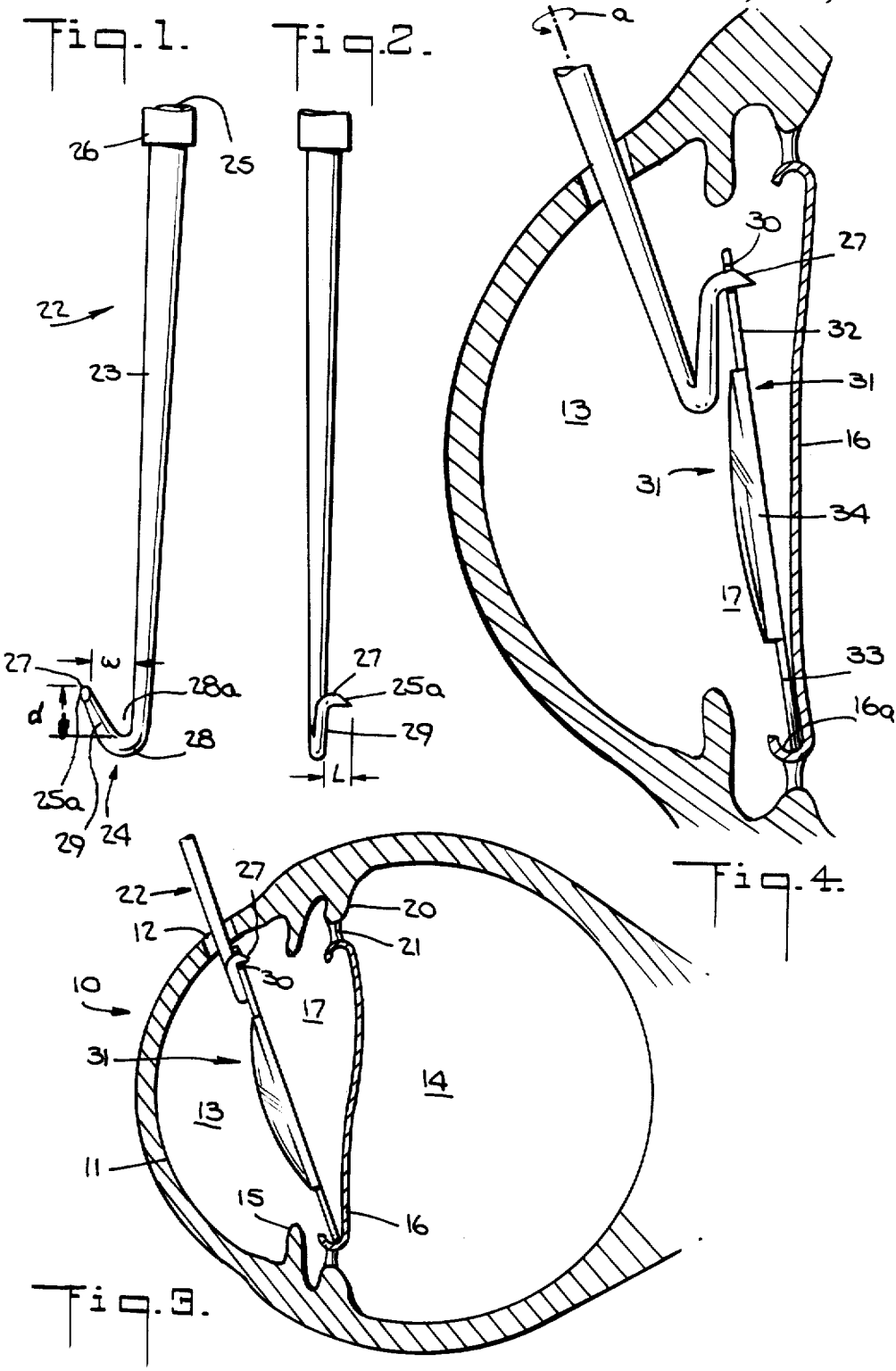

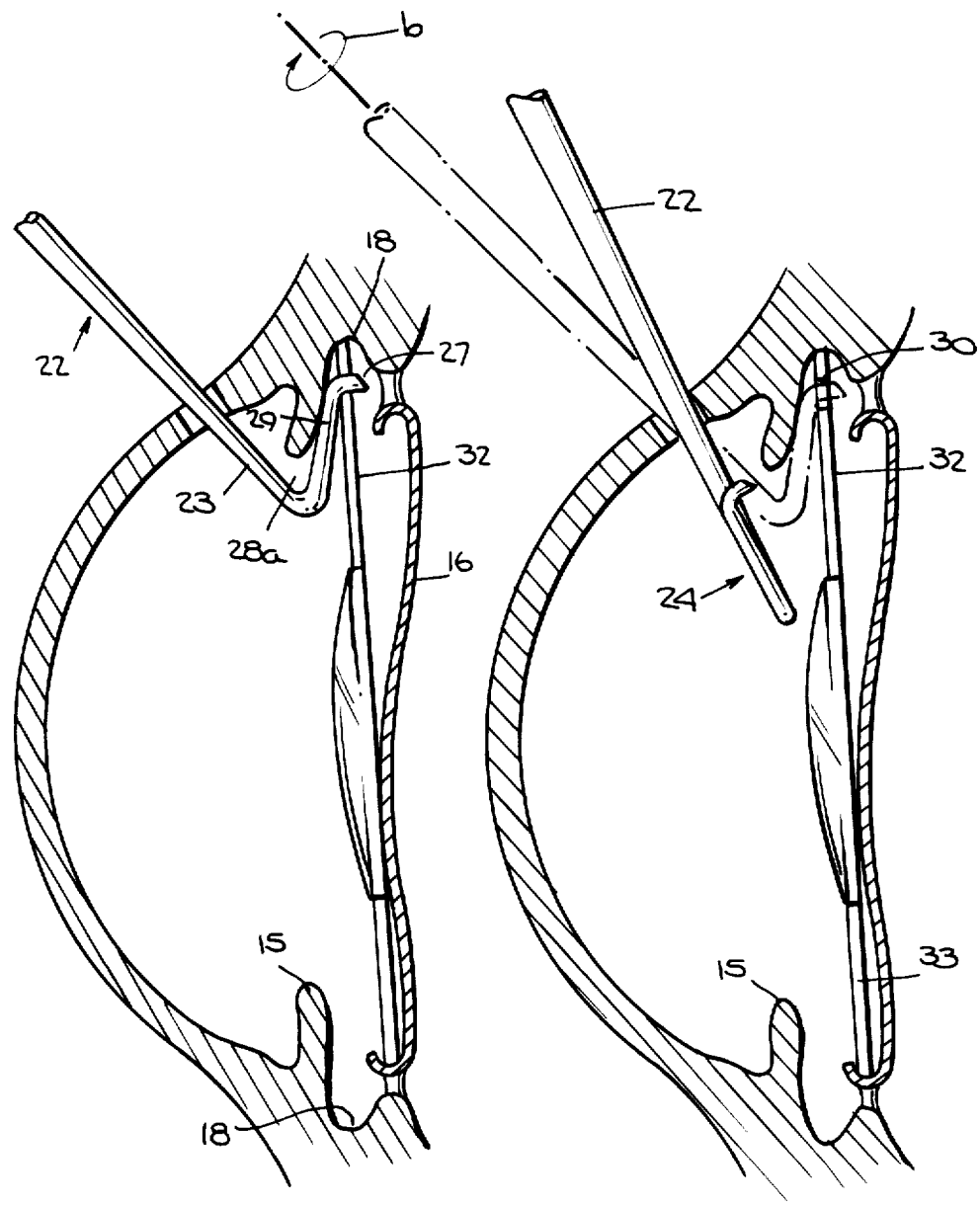

SURGICAL INSTRUMENT FOR AND METHOD OF INSERTING A POSTERIOR CHAMBER LENS IN AN EYE

This invention relates to surgical instruments and to methods for inserting an intraocular lens in an eye. More particularly, the invention relates to surgical instruments of the type having a hook at the end thereof and to methods of seating an intraocular lens in the posterior chamber of an eye using such hooked instrument.

Conventionally, in the seating of posterior chamber intraocular lenses such as, for example, the lenses described in my copending patent application Ser. No. 465,573, after the first, or lower, of the pair of haptics, or position-fixation members, is seated in a lower portion of the posterior chamber, the surgeon depresses the second or upper haptic toward the first so that it too can be passed through the pupil. Once the second haptic is on the posterior side of the iris it is allowed to expand toward its normal undeformed condition for seating thereof in an upper portion of the posterior chamber. With conventional surgical instruments this is a complicated procedure for the surgeon since, if the upper haptic is merely released once it is behind the iris it will tend to spring back into its original undeformed condition which not only may cause injury to membranes in the posterior chamber of the eye but additionally will be very difficult to position for proper seating. If, on the other hand, the known surgical instruments are used to permit the upper haptic to only slowly return to its seating position, it is difficult to keep such instruments from touching the iris, risking damage to that membrane.

It is an object of the present invention, therefore, to provide a new and improved surgical instrument which avoids one or more of the disadvantages of prior such instruments.

It is another object of the invention to provide a new and improved surgical instrument for permitting the upper haptic to slowly return to its original undeformed condition.

It is still another object of the invention to provide a new and improved surgical instrument which can be easily disengaged from the upper haptic after the latter has returned substantially to seating position thereof without causing injury to the eye.

It is a still further object of the invention to provide a new and improved surgical instrument which can give the surgeon control over the position of the upper haptic during seating thereof.

It is another object of the invention to provide a new and improved method of seating an intraocular lens in the posterior chamber of an eye which avoids one or more of the disadvantages of prior such methods.

It is a concomitant object of the invention to provide a new and improved method of seating an intraocular lens in the posterior chamber of an eye while retaining substantial control over the positioning of the haptics.

In accordance with the invention, a surgical instrument for seating an intraocular lens in the posterior chamber of an eye comprises a longitudinally extending shank portion having a hooked end portion terminating in a transverse tip portion. The hooked end portion comprises a curved neck portion extending from the shank and a tip portion extending from the end of the curved neck portion in a direction transverse to the plane containing the shank and the neck portion. The tip portion is adapted to be inserted into the small opening usually provided in the upper haptic of conventional posterior chamber intraocular lenses, for displacing the upper haptic toward the lower haptic during the insertion procedure. The instrument may be hollow, with an opening at its distal end so as to permit the injection of fluid into the eye in a manner similar to a hypodermic needle.

Also in accordance with the invention, a method of inserting and seating an intraocular lens in the posterior chamber of an eye comprises inserting the hooked end portion of an instrument having a longitudinal shank portion through an opening in the eye. The instrument has at one end of the longitudinally extending shank portion a hooked portion having a tip. The method also includes engaging one of the haptics of the intraocular lens with the hooked portion and moving the instrument in a direction to seat the engaged haptic in the posterior chamber. The method further includes disengaging the tip of the hooked portion from the aforesaid haptic after substantially seating the latter and withdrawing the hooked portion from the posterior chamber. The method may also include injecting a fluid into the posterior chamber through the open distal end of the tip portion of the instrument just prior to withdrawal thereof from its engagement with the haptic.

For a better understanding of the present invention, together with other and further objects thereof, reference is made to the following description, taken in conjunction with the accompanying drawings, and its scope will be pointed out in the appended claims.

Referring now to the drawings:

BRIEF DESCRIPTION OF THE DRAWINGS

FIG. 1 is a front elevational view of the surgical instrument in accordance with the invention;

FIG. 2 is a side elevational view of the surgical instrument of FIG. 1;

FIG. 3 is a fragmentary sectional view of a human eye with a surgical instrument in accordance with the invention shown in engagement with an intraocular lens whose lower haptic is seated in the posterior capsule;

FIG. 4 is an enlarged fragmentary sectional view of a human eye showing the intraocular lens in engagement with a surgical instrument in accordance with the invention while passing the upper haptic through the pupil of the eye;

FIG. 5 is an enlarged fragmentary sectional view of a human eye with the surgical instrument in accordance with the invention in position seating the upper haptic of the intraocular lens in the ciliary sulcus of the posterior chamber;

FIG. 6 is an enlarged fragmentary sectional view of the human eye and the surgical instrument according to the invention showing the disengagement of the surgical instrument from the upper haptic.

Referring now particularly to FIGS. 3 through 6 of the drawings, a human eye 10 is represented in section, with portions omitted for the sake of clarity. The eye 10 includes a cornea 11 having an opening 12 therein made by the surgeon. Anterior chamber 13 and posterior chamber 14 are defined by the position of the iris 15. A membrane, or posterior capsule 16, which remains after extracapsulary removal of a cataracted natural lens therefrom, is normally connected to ciliary body 20 by a plurality of zonules 21. The iris defines a central opening, or pupil 17, represented in the drawings in dilated condition.

Referring particularly to FIGS. 1 and 2, a surgical instrument 22 constructed in accordance with the invention comprises a longitudinally extending shank portion 23 and a hooked portion 24, which preferably is curved, at one end of the longitudinally extending shank portion 23. The surgical instrument 22 may be formed from a conventional hypodermic needle and therefore has a bore 25 extending longitudinally along the length thereof from a connector portion 26 at one end of the longitudinal portion and adapted to be connected to a hypodermic siringe, to the tip 27 at the distal end of the surgical instrument. The connector 26 is of conventional type for attachment of a hypodermic needle to a siringe and is therefor not shown in detail. The hook portion 24 of the surgical instrument according to the invention comprises first and second limb portions 28 and 29. As represented in FIGS. 1 and 2, the first limb portion 28 extends transversely to the longitudinal shank portion 23 and together with second limb portion 29 forms a throat 28a having a width "w" of about 0.030 to 0.070, inches but preferably about 0.058 inches.

Second limb 29, first limb 28 and shank 23 preferably lie substantially in a plane, i.e. the plane of the paper as seen in FIG. 1, with second limb 29 preferably inclined with respect to shank 23 at an angle of approximately 45°. Tip portion 27 extends transversely, preferably at substantially a right angle, to the plane in which the shank portion 23 and the limb portions 28 and 29 are located, a distance "l" of approximately 0.020 to 0.040 inches, preferably about 0.030 inches. The tip portion 27 is preferably the tip of a hypodermic needle and thus preferably has an opening 25a therein. Second limb portion 29 has a length upwardly from the first limb 28 such that the depth "d" of throat 28a is approximately 0.050 to 0.120 inches and preferably distance "d" is about 0.085 inches.

The method of using the instrument in accordance with the present invention comprises inserting the instrument 22 through the opening 12 in the eye and placing the tip 27 into an opening 30 of intraocular lens 31 previously inserted in the eye as represented in FIG. 3. Posterior chamber lens 31 includes an optic 34 and a pair of position fixation members 32 and 33 at opposite sides of the optic. The upper position fixation member 32 conventionally has an opening 30 for insertion of a surgical tool. Of course, instead of having an opening 30 the intraocular lens may merely have a depression or indentation (not shown) in the region of its upper seating surface, adapted to be engaged by the tip 27 of instrument 22.

Preferably the lens 31 is inserted through the corneal incision 12 in conventional manner and the lower position-fixation member 33 thereof is passed through the pupil and seated in the lower cul-de-sac 16a formed by the posterior capsule 16. Thereafter, as seen in FIG. 3, the instrument 22 is inserted through opening 12 and the tip 27 of the instrument is inserted in the opening 30 of the upper position fixation member 32 of the lens. The surgeon then moves the instrument generally axially, thus compressing position-fixation members 32 and 33 until they are sufficiently compressed so that the lens will fit through the pupil 17, as seen in FIG. 4. With a slight rotational movement of the instrument 22 about its own axis in the direction of arrow "a", FIG. 4, together with a reverse axial movement of the instrument in a direction away from the lower position-fixation member (FIG. 5), the surgeon can control the position-fixation member 32 of the lens as it expands into the seating condition thereof shown in FIG. 5. In this position the upper seating portion of the upper position-fixation member 32 is seated in the ciliary sulcus behind the iris and the throat 28a of the instrument is sufficiently deep to permit the iris 15 to be located within the confines of neck portion 24 without substantial contact of the instrument 22 with the iris. In this position of instrument 22 the first limb portion 28 extends through the pupil 17, the second limb portion 29 extends from the end of the first limb portion a distance sufficient for tip portion 27 to reach substantially to the ciliary sulcus 18 of the eye while the shank 23 of the instrument is substantially adjacent the anterior surface of the iris.

A slight rotational movement of the instrument 22 about its own axis in the direction of arrow "b" in FIG. 6, i.e. in a direction reverse to the prior rotational movement, acts to withdraw the tip 27 from the opening 30 in the lens as represented in FIG. 6 in going from the dashed-line to the solid-line postion. During this procedure the upper position-fixation member 32 of the lens will tend to maintain its seated position. Since the membranes in the eye are resilient, the shank 23 of the instrument may be moved so that it engages the anterior surface of the iris and acts to press a portion of the iris against portions of the intraocular lens behind it. While the lens is thusly prevented from movement in anterior direction both by position-fixation member 32 being seated and by the shank 23 engaging the iris, the reverse rotational movement of the instrument 22 will permit withdrawal of the tip 27 from the opening 30. Thereafter, with an axial downward movement, i.e. again in a direction toward the lower position fixation member 33 of the lens, the surgeon can move the instrument 22 so that its hook portion 24 will clear the iris and may be withdrawn through the pupil 17 as seen in solid line in FIG. 6. It should be understood that the FIG. 6 representation is diagrammatic only and for the sake of clarity does not show a region of the iris in contact with shank 23 of the instrument while the tip 27 is relatively rotationally moved in a direction into the posterior side of the flexible iris for withdrawal of the tip from the opening 30.

Preferably, a material such as Helon is injected through the bore 25 and the distal opening 25a of instrument 22 into the chamber formed behind the iris when the procedure has approached the stage shown in FIG. 5 of the drawings. The Helon will temporarily fill the space behind the iris and tend to push the iris in anterior direction so as to temporarily enlarge the posterior chamber of the eye bounded by the posterior side of the iris 15 on the one hand and the posterior capsule 16 on the other hand.

While there has been described what is at present considered to be the preferred embodiment of this invention, it will be obvious to those skilled in the art that various changes and modifications may be made therein without departing from the invention, and it is, therefore, aimed to cover all such changes and modifications as fall within the true spirit and scope of the invention.

What is claimed is:

1. A surgical instrument for seating an intraocular lens in the posterior chamber of an eye, comprising:
   a longitudinally extending shank portion;
   a hook portion at one end of said longitudinally extending shank portion having a neck portion and a tip portion, said tip portion extending transversely to the plane containing said shank portion and said neck portion.

2. A surgical instrument in accordance with claim 1 in which said neck portion forms a throat between said shank and said tip portions adapted to accommodate the iris of an eye therein.

3. A surgical instrument in accordance with claim 2 in which the width of said throat is about 0.030–0.070 inches.

4. A surgical instrument in accordance with claim 3 in which the depth of said throat is about 0.050–0.120 inches.

5. A surgical instrument in accordance with claim 4 in which said tip is pointed and the length of said tip is about 0.020–0.040 inches.

6. A surgical instrument in accordance with claim 1 in which said neck portion is curved.

7. A surgical instrument in accordance with claim 1 in which said shank portion and said hook portion have a bore extending therethrough and said tip portion has an opening communicating with said bore.

8. A surgical instrument in accordance with claim 1 in which said neck portion forms a throat between said tip portion and said shank portion and the size of said neck portion is such that when the instrument is positioned with its shank portion in the anterior chamber of the eye and its tip portion in the posterior chamber of the eye said tip portion will substantially reach to the ciliary sulcus.

9. A surgical instrument in accordance with claim 1 in which said shank portion extends in a first direction from the other end to said one end thereof and in which said neck portion has a first limb portion extending generally transversely to said shank portion and a second limb portion extending from the end of said first limb portion to said tip portion in a second direction generally opposite to said first direction of said shank portion a distance sufficient for said tip portion to reach substantially to the ciliary sulcus of an eye when said shank portion is substantially adjacent the anterior surface of the iris of the eye and said first limb portion extends through the dilated pupil of the eye without substantially distorting the pupil with said first limb portion.

10. A surgical instrument for seating an intraocular lens in the posterior chamber of an eye, comprising:
a longitudinally extending shank portion;
a hook portion at one end of said longitudinally extending shank portion having a neck portion and a tip portion;
said neck portion having a first limb portion adapted to extend through the pupil, and a second limb portion connected to said first limb portion and adapted to extend along the posterior side of the iris;
said second limb portion having an end adapted to extend into substantial proximity with an inner peripheral surface of the posterior chamber of the eye;
said tip portion extending in cantilever relation from said end of said limb portion.

11. A method of seating an intraocular lens in the posterior chamber of an eye comprising:
inserting an intraocular lens into the eye and seating the lower haptic of the lens in the posterior chamber;
inserting a portion of an instrument having a longitudinally extending shank through an opening in the eye, said instrument having at one end of said longitudinally extending shank a hook portion having a neck and a tip at the end of said neck transverse to said neck;
moving the tip into engagement with the upper haptic of the lens still in the anterior chamber; and
moving the instrument substantially axially thereof to compress said haptics until the upper haptic fits through the pupil of the eye;
moving the instrument to move the upper haptic through the pupil into the posterior chamber;
moving the instrument in reverse substantially axial direction allowing the haptics to expand toward their undeformed condition, so as to at least substantially seat the upper haptic in the posterior chamber while embracing the iris in the neck of the instrument;
rotating the instrument about its axis to withdraw the tip from the upper haptic; and
moving the instrument in said first mentioned axial direction until the tip is in registry with the pupil so that it may be withdrawn through the pupil from the posterior chamber.

12. A method in accordance with claim 11 further comprising injecting a fluid through a bore in the instrument opening at the tip thereof, when said tip is in the posterior chamber of the eye, for temporarily pushing the iris in anterior direction so as to temporarily enlarge the posterior chamber during seating of the upper haptic.

* * * * *